United States Patent
Burton

(10) Patent No.: US 6,906,229 B1
(45) Date of Patent: Jun. 14, 2005

(54) PROCESS FOR HYDROLYZING DI-ISOPROPYL ETHER TO ISOPROPYL ALCOHOL BY CATALYTIC DISTILLATION USING A SOLID ACID CATALYST

(75) Inventor: Paul E. Burton, Baton Rouge, LA (US)

(73) Assignee: ExxonMobil Chemical Patents, Inc., Houston, TX (US)

(*) Notice: Subject to any disclaimer, the term of this patent is extended or adjusted under 35 U.S.C. 154(b) by 0 days.

(21) Appl. No.: 09/515,428

(22) Filed: Feb. 29, 2000

(51) Int. Cl.$^7$ .................. C07C 29/10; C07C 29/00; C07C 29/04
(52) U.S. Cl. .............. 568/907; 568/895; 568/896; 568/897; 568/898; 568/899; 568/900
(58) Field of Search ................ 568/895, 896, 568/897, 898, 899, 900, 907

(56) References Cited

U.S. PATENT DOCUMENTS

| | | | |
|---|---|---|---|
| 1,602,846 A | 10/1926 | Burke | |
| 2,045,785 A | 6/1936 | Lewis | 260/156 |
| 2,105,508 A | 1/1938 | Rosen et al. | 260/151 |
| 2,115,874 A | 5/1938 | Rehm | 260/156 |
| 2,216,931 A | 10/1940 | Archibald et al. | 260/614 |
| 2,403,672 A | 7/1946 | Matuszak | 260/683 |
| 2,533,808 A | 12/1950 | Howlett et al. | 260/639 |
| 2,609,400 A | 9/1952 | Amick, Jr. | 260/639 |
| 2,638,440 A | 5/1953 | Drout, Jr. et al. | 202/39 |
| 2,663,679 A | 12/1953 | Drout, Jr. | 202/39 |
| 2,668,863 A | 2/1954 | Norris | 260/643 |
| 2,759,237 A | 8/1956 | Scovill et al. | 24/216 |
| 2,839,588 A | 6/1958 | Parker | 260/635 |
| 2,994,721 A | 8/1961 | Wilson et al. | 260/614 |
| 3,634,534 A | 1/1972 | Haunschild | 260/677 |
| 3,634,535 A | 1/1972 | Haunschild | 260/677 |
| 4,079,068 A | 3/1978 | Hatzel et al. | 260/346 |
| 4,161,429 A | 7/1979 | Baiel et al. | 203/18 |
| 4,219,685 A | 8/1980 | Savini | 568/917 |
| 4,232,177 A | 11/1980 | Smith, Jr. | 585/324 |
| 4,250,328 A | 2/1981 | Fujita et al. | 560/205 |
| 4,405,822 A | * 9/1983 | Bezman | 568/899 |
| 4,447,668 A | 5/1984 | Smith, Jr. et al. | 585/639 |
| 4,471,142 A | 9/1984 | Burton et al. | 568/696 |
| 4,581,475 A | 4/1986 | Neier et al. | 568/907 |
| 5,043,486 A | 8/1991 | Siskin et al. | 568/907 |
| 5,204,064 A | 4/1993 | Smith, Jr. | 422/106 |
| 5,345,006 A | 9/1994 | Smith, Jr. | 568/899 |
| 5,571,387 A | 11/1996 | Marker et al. | 203/41 |
| 5,585,527 A | 12/1996 | Marker | 568/835 |
| 5,689,014 A | 11/1997 | Frey et al. | |
| 5,705,712 A | 1/1998 | Frey et al. | |

FOREIGN PATENT DOCUMENTS

GB     535111     11/1939

OTHER PUBLICATIONS

"Propyl Alcohols," Kirk–Othmer, Encyclopedia of Chemical Technology, Fourth Edition., vol. 20, pp. 216–240, 1996.
"Propyl Alcohols" Propyl Alcohols (Isopropyl); Kirk Othmer Encylopdia of Chemistry, Fourth Edition, vol. 20, p. 216, pp. 223–236.

* cited by examiner

*Primary Examiner*—Elvis O. Price
(74) *Attorney, Agent, or Firm*—Andrew B. Griffle

(57) ABSTRACT

The invention relates to the production of isopropyl alcohol from di-isopropyl ether by catalytic distillation. The process solves, in particular, problems associated with the Sulfuric Acid Process.

14 Claims, 1 Drawing Sheet

US 6,906,229 B1

PROCESS FOR HYDROLYZING DI-ISOPROPYL ETHER TO ISOPROPYL ALCOHOL BY CATALYTIC DISTILLATION USING A SOLID ACID CATALYST

FIELD OF THE INVENTION

The present invention is directed to a process for hydrolyzing di-isopropyl ether to isopropyl alcohol by catalytic distillation.

BACKGROUND OF THE INVENTION

Isopropyl alcohol ("IPA"; also known as isopropanol, 2-propanol, dimethylcarbinol, and sec-propyl alcohol) is an important commercial product. IPA finds use as a feedstock for other compounds, such as acetone, methyl isobutyl ketone, and isopropylamine, as a solvent in consumer products such as cosmetics and in industrial processes such as extractions, and also in medical uses such as disinfectants, antiseptics, liniments, and tinctures.

Large volumes of alcohols and ethers are produced annually by the catalytic hydration of olefins, particularly by the Indirect Hydration Process or Acid Catalyzed Hydration Process, where mono-olefins are hydrated in the presence of polybasic mineral acids. Chief among these processes is the "Sulfuric Acid Process", in which the selected olefin feed is absorbed in a concentrated sulfuric acid stream to form an "extract" containing the corresponding alkyl ester of the sulfuric acid. Thereafter, water is admixed with the ester-containing extract to hydrolyze the ester and form the desired alcohol and ether, which are then recovered, generally by stripping with steam or some other heating fluid in an alcohol generator. See, for instance, Kirk-Othmer, *Encyclopedia of Chemical Technology*, 4th Ed., Vol. 20, pp. 216–236; U.S. Pat. Nos. 2,663,679; or 2,638,440.

The di-isopropyl ether ("DIPE"; often referred to as "isopropyl ether" or "IPE") produced in these conventional processes is much less valuable than the IPA co-product. Accordingly, numerous proposals have been made to increase the IPA/DIPE ratio.

U.S. Pat. No. 2,105,508 relates to a process for producing DIPE by absorption of propylene. The extract liquid is passed from the absorption tower and introduced, after the addition of water or steam (to compensate for the water reacting to form the ether) to one of a series of ether generating pots, each equipped with steam coils. A vaporous product containing DIPE and IPA, is withdrawn, treated in a soda scrubber and passed to a distillation tower. Unreacted propylene is recovered as overheads in the distillation tower and can be recycled to the absorber. A sidestecam of condensed ether vapors is withdrawn from the top of the distillation tower, and an IPA-containing liquor is formed as bottoms product. The alcoholic bottoms is then, with or without removal of water, refluxed to the ether generating pots or passed to further refining as alcohol. Spent acid liquor remaining in the ether generating pots is recycled to the absorber. Reflux of the alcoholic bottoms to the ether generating pots is said to permit more accurate control of the ether generating conditions therein and to permit the acid to be concentrated to a higher strength before recycle to the absorber.

British Pat. No. 535,111 relates to a process for manufacture of ethers from olefins in which the sulfuric acid extract liquid is removed from the absorbing tower and is partially stripped in a stripping tower to form an ether-alcohol overhead mixture and a partially stripped extract as bottoms. The overhead mixture is passed to a separate tower for separation of the ether and to form an alcohol-containing bottoms. These alcohol-containing bottoms from the last tower are combined with the partially stripped extract, and sufficient water is added to make up that used in the formation of the ether. The resulting liquid stream is then recycled as the absorbate to the top of the absorbing tower.

U.S. Pat. No. 2,216,931 relates to aliphatic ethers including DIPE. According to the patent, such ethers are produced by a process in which the sulfuric acid extract containing olefin is split into two portions: a first portion is passed, after addition of water, to a stripping tower for formation of a vaporous overhead comprising the corresponding alcohol; and a second portion is fed directly to a reaction tower, together with the vaporous alcohol overhead formed in the stripping tower. In the reaction tower a liquid overhead stream is withdrawn and then passed to a generator for formation of vapors, which are then fed into a fractionating tower for recovery of the DIPE product as overhead and to form a bottoms product comprising IPA. This alcohol bottoms is then admixed with the stream containing the alcohol vapors withdrawn from the stripping tower for feed to the reaction tower.

In U.S. Pat. No. 2,533,808 the extract liquid is diluted with water and then passed to an alcohol generator for formation of dilute sulfuric acid as bottoms and to form overhead vapors comprising IPA and DIPE. This vapor product is then treated to separate the IPA as product and to recover the DIPE, which is recycled to the absorbing stage. In this process, the production of IPA can be increased by the recycle of the DIPE.

In U.S. Pat. No. 2,609,400 the propylene sulfuric acid extract liquid is stripped, without dilution with water, in a generator-stripper to form a mixture of ether and alcohol vapors. The partially stripped acid extract is then admixed with sufficient water (which can be added as steam via the steam injection into the stripper) to replace the water consumed in forming the alcohol and ether thus removed. Careful regulation of the extract temperature, steam temperature and pressure, and use of hot stripping gas is required to so control the heat balance of the generator-stripper to avoid dilution of the acid. Partially stripped acid extract is withdrawn from the generator-stripper and recycled to the olefin absorber, together with make-up acid as required. The ether/alcohol vapors withdrawn from the generator-stripper are scrubbed with a caustic solution to remove entrained acid, and the acid-free vapors are then condensed. The condensate, which comprises predominantly isopropyl alcohol, can be distilled to separate DIPE, which can be at least in part admixed with the partially stripped acid extract for recycle to the absorber.

In U.S. Pat. No. 2,994,721 the extract is passed into an ether generation zone from which vapors comprising predominantly DIPE are withdrawn as overhead. The remaining liquids are then diluted with water and fed to an alcohol generator for formation of overhead vapors comprising IPA and some DIPE. Dilute acid is withdrawn as bottoms product from the alcohol generator for concentration and subsequent recycle to the absorbing stage.

In German Offenlegungsschrift No. 2,759,237 propylene is absorbed in sulfuric acid to form an extract which is then treated to liberate the ether and alcohol. After separation of the alcohol, the ether is recycled to make more alcohol.

None of the foregoing processes are readily adaptable to vary appreciably the ratios of co-product isopropyl alcohol and di-isopropyl ether. In addition, most suffer in that recycling invariably results in recycling of impurities which have a negative effect on the process sooner or later.

A greater increase in the IPA/DIPE ratio is taught in U.S. Pat. No. 4,471,142. Propylene is contacted in an absorbing zone with aqueous sulfuric acid for formation of a liquid extract comprising sulfuric acid containing absorbed propylene values (i.e., all species in the mixture containing propyl or propylene moieties). The extract is contacted with a carefully controlled amount of water and the resulting hydrated extract is passed to an ether generating zone. Here, the hydrated extract is treated to liberate vapors containing DIPE and to form a liquid bottoms product comprising a depleted sulfuric acid extract containing absorbed propylene values and having a sulfuric acid concentration at least equal to the acid concentration in the extract liquid. The depleted extract is divided into two streams. The first stream is passed to an alcohol generator, after addition of water, to form an overhead product comprising predominantly isopropyl alcohol and a bottoms product comprising a dilute sulfuric acid stream. The second portion of said bottoms product is recycled to the absorbing zone. However, this method still produces DIPE in the amount of about 10% by weight.

Numerous patents are directed to the production of alcohols from ethers wholly separate from these olefin hydration processes. For instance, U.S. Pat. No. 1,602,846 relates to a process for converting methyl ether, obtained by the hydrolytic decomposition of methyl chloride, to methyl alcohol by reacting the former with steam over a refractory oxide in a tube. There is no distillation contemplated. Rather, methyl alcohol is recovered from the cooled reaction mixture by scrubbing with water. Furthermore, the patent explains that the process disclosed therein is "not applicable to all ethers".

U.S. Pat. No. 2,115,874 teaches that the process taught in the aforementioned U.S. Pat. No. 1,602,846 is inoperative for the treatment of ethyl ether and higher ethers. This patent teaches an appropriate catalyst for vapor phase hydration of alpihatic ethers. The aliphatic ether is mixed with water vapor and the mixture of reactants is passed over a catalytic mass in a reaction zone at elevated temperatures. After leaving the reaction zone, the liquid condensate is fractionally distilled to separate the alcohol from the ether.

U.S. Pat. No. 3,634,534 teaches a process specifically envisioned to be used to separate linear olefins from tertiary olefins. A mixture is fed to a first distillation column reactor wherein tertiary olefins are reacted with an alcohol (such as methanol). Alcohol is removed from the lower part of the second distillation column reactor and recycled back to the first distillation column reactor.

U.S. Pat. No. 4,250,328 teaches separation of an ester from a reaction mixture comprising an ester, alcohol, organic acid, and water. The unreacted alcohol is removed as an ester-water azeotrope overhead.

Other processes include: U.S. Pat. No. 4,581,475, which teaches producing a lower aliphatic alcohol by splitting ethers over a catalyst in the presence of water; U.S. Pat. No. 5,043,486 teaching a method of producing alcohols from ethers without the use of catalysts; and yet another process is taught by U.S. Pat. No. 5,571,387, using an apparatus comprising a distillation zone and adsorption zone.

of the aforementioned patents teach a process involving utilizing a catalyst set within a distillation column, i.e., "catalytic distillation". It has been suggested in the past to apply catalytic distillation to various processes, such as butene isomerization (U.S. Pat. No. 2,403,672); the hydrolysis of low molecular weight olefin oxides to produce monoalkylene glycols (see U.S. Pat. No. 2,839,588); the production of methyl tertiary butyl ether (MTBE; see U.S. Pat. No. 3,634,535); and the production of tetrahydrofuran (see U.S. Pat. No. 4,079,068). In general the term "catalytic distillation" (or "reactive distillation") covers any distillation or fractionation process or apparatus wherein the distillation column contains a catalyst for chemical conversion during separation.

Recognized advantages attributed to the catalytic distillation concept include a decrease in the capital cost of the plant needed to perform the process, the ability to achieve a higher degree of conversion, and the ability to perform processes which formerly were performed only in a batch type operation on a continuous basis.

The use of an aqueous acid contacting a substrate within a distillation column is taught in U.S. Pat. No. 2,045,785. In this process, steam and ether are introduced together at the bottom of a distillation column. An aqueous acid solution is introduced at the top of the distillation column. A "catalytic contact zone" is formed by the distillation column packing, and the alcohol is recovered in the acid liquor, which is then sent to a distillation column where the alcohol is removed overhead, along with unreacted ether. This mixture is then sent to another distillation column, where the alcohol and ether are separated. It is taught that "if the catalyst is allowed to continuously concentrate", a large percentage of olefins results. The aspect of avoiding concentration of the catalyst is explicitly claimed. In a second embodiment, the reactor distillation column is at such a temperature that the alcohol and unreacted ether are taken overhead, and the acidic liquor is taken as bottoms.

U.S. Pat. No. 4,232,177 teaches a method using catalytic distillation wherein a mixed feed stream of isobutene and normal butene is fed into the lower end of a distillation column and methanol is fed into the upper end of the same column, the column being packed with a fixed bed catalyst. Methyl tertiary butyl ether (MTBE) is the product.

U.S. Pat. No. 4,447,668 teaches passing a feed stream comprising alkyl tertiary butyl ether (such as MTBE) over a fixed bed catalyst to produce an isoolefin and alcohol. There is no water (or steam) used in the catalytic distillation column. The alcohol is separated from the dissociation product stream as a bottom fraction, and the alcohol depleted product stream is then contacted with a second catalyst to form diisobutene.

U.S. Pat. Nos. 5,204,064 and 5,345,006 describe a method and apparatus for conducting catalytic distillation which allows for maintaining a liquid level in selected portions of the catalyst bed. In one embodiment, t-butyl alcohol is produced by the hydration of isobutylene Unreacted butylene, water, and inerts (e.g., other C4s) are taken overhead and TBA is recovered as bottoms.

U.S. Pat. No. 5,585,527 discloses a process for separating a first component from a second component of a process stream in a "single vessel" including a "membrane separation zone" and a distillation zone. The distillation zone may contain a "separation catalyst". Specific applications envisioned include the separation of IPA and water in a process including forming DIPE from IPA. The patent also discloses the production of IPA from DIPE in an "IPA reactor that may be a stirred tank or fixed bed reactor. The effluent stream from this IPA reactor that is put through the "single vessel" reactor of the invention.

However, none of these address production of IPA by catalytic distillation and none teach anything about improving hydration of olefins processes. Thus, the aforementioned problems concerning the IPA/DIPE ratio still remain to be solved. Moreover, there still remains the need for an efficient means of producing IPA from DIPE.

SUMMARY OF THE INVENTION

The present invention relates to treatment of a stream including di-isopropyl ether (DIPE) from the catalytic hydration of olefins. The stream is fed below the acid catalyst-containing trays in a catalytic distillation tower and water is fed to the tower above the catalyst. As water and DIPE contact the catalyst, the DIPE is hydrolyzed to IPA, which is removed from the bottom of the tower as a dilute IPA/water stream. By avoiding the conventional recycling of DIPE, which contains all the light and heavy byproducts from the Sulfuric Acid Process, it avoids additional byproduct formation, prolongs the life of the catalyst used in the hydration of olefins, and improves the ratio of IPA to DIPE produced in the overall process.

The present invention relates more generally to the production of IPA from DIPE by the catalytic hydration of the latter in a catalytic distillation column containing the solid acid catalyst. The IPA is removed as bottoms, and the overhead, which may contain a minimum boiling azeotrope of IPA, water, and DIPE, along with lights, water-volatile heavy material, and any propylene formed during the distillation reaction, are processed as described below in more detail.

Thus, it is an object of the present invention to increase the amount of IPA recovered in a Hydration of Olefins Process, particularly the Sulfuric Acid Process, without a negative effect on other parts of the process.

It is a further object of the invention to provide a continuous process, not limited by chemical equilibrium, for the conversion of DIPE to IPA, wherein reaction products are continuously separated from the reactants and removed from the reaction zone by functional distillation performed concurrently with the reaction.

It is yet another object of the invention to provide a modification of the Sulfuric Acid Process whereby at least a portion of the stream comprising DIPE, which is typically recycled in the process, is instead sent to a catalytic distillation tower whereby it is converted to IPA in high yield.

These and other objects, features, and advantages of the present invention will become apparent as reference is made to the following detailed description of the preferred embodiments and accompanying figures.

DETAILED DESCRIPTION OF THE INVENTION

Figure 1:
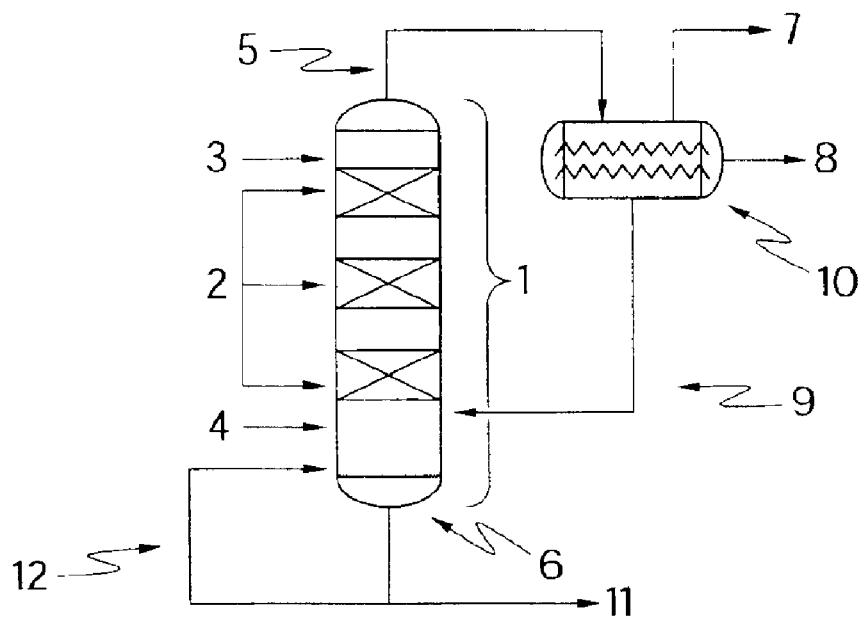
FIG. 1 is a schematic illustrating a preferred embodiment of the invention, where DIPE enters below the catalyst trays, water enters above the trays, and IPA is taken off as bottoms.

Referring now in more detail to the preferred embodiment illustrated in FIG. 1, catalytic distillation tower or column 1 comprises one or more catalyst trays 2 and includes an intake for water 3 and feed stream 4, comprising DIPE from the Sulfuric Acid Process. The overheads, which may comprise unreacted DIPE, lights, water-volatile heavies, propylene, and various azeotropes including a IPA/DIPE/water azeotrope, are taken off at 5, and the bottoms, comprising dilute IPA/water mixture, are taken off at 6.

Figure 2:
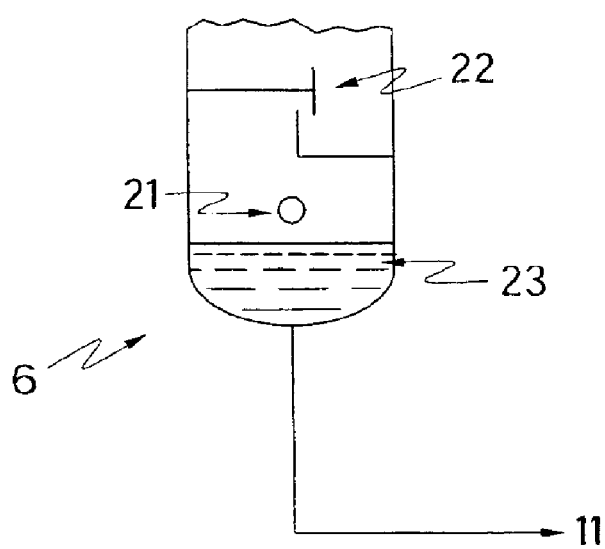
FIG. 2 is an alternative view of the bottom portion of the reactor according to the invention, wherein steam is introduced below the trays.

Water feed 3 is preferably provided above the trays, as shown in FIG. 1, but may also be provided below the trays as steam (inlet 21, as shown in FIG. 2, described below in more detail). A combination of water and steam may be used. Water and steam may also be provided at various other points in column 1, depending on packing arrangements, as may be determined by one of ordinary skill in the art in possession of the present disclosure.

In the most preferred embodiment, DIPE feed 4 is from the Sulfuric Acid Process. In another preferred embodiment, the feed 4 may be from any process comprising the catalyzed hydration of olefins, including the Direct Hydration Process in which the olefin is hydrated in the presence of solid catalyst such as phosphoric acid. However, the DIPE feed may be from any source.

Although a plurality of trays 2 are shown in FIG. 1, any number of trays may be used from one to several hundreds, depending also on the height of the column. In a more preferred embodiment about fifty trays are used. Each tray may contain catalyst. However, it may be beneficial that some of the trays do not contain catalyst. For instance, in a preferred embodiment, fractionation trays not containing catalyst are present above and below the trays containing catalyst.

In an even more preferred embodiment, a fixed bed catalyst packing serves as both catalyst and distillation packing, such as in the form of rings (e.g., Raschig or Pall rings), saddles, balls, irregular pieces, sheets, tubes, spirals, packed in bags, plated on grills or screens, reticulated polymer foams, and the like. Another preferred embodiment is to provide the catalyst as a resin, which may be in granular or bead form, which may be placed in the distillation column 1 in numerous ways, as is known per se in the art.

The catalyst used herein may be any solid material which is recognized for hydrolyzing ethers to the alcohol, such as solid acidic catalyst that can be used for olefin hydration. Examples include acidic ion exchange resins, such as Amberlyst® 15, supported mineral acids, such as phosphoric acid on a solid support, acidic zeolites, acidic alumina, and the like. A specific preferred example is alumina treated with aluminum sulfate (e.g., see U.S. Pat. No. 2,115,874).

According to the invention, the reaction of DIPE and water in contact with the catalyst produces IPA according to Equation (1) below.

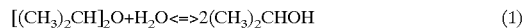

$$[(CH_3)_2CH]_2O + H_2O \Longleftrightarrow 2(CH_3)_2CHOH \qquad (1)$$

This an equilibrium reaction but is driven to the right in the catalytic distillation tower by removal of the product(s). A small amount of propylene is also produced. There is possibly some oligomerization of propylene to $C_6$ and higher oligomers, which can be minimized by increasing the amount of water present relative to DIPE via control of feed streams 3 and 4 and/or the concentration of DIPE in feed stream 4.

One of the complicating factors in driving the reaction is that IPA and DIPE form numerous azeotropes (see Kirk-Othmer, supra), including a minimum boiling ternary azeotrope of IPA/DIPE/water, which is taken off in overheads 5. Along with this azeotrope is unreacted DIPE and also, when feed stream 4 is from the Sulfuric Acid Process, there will be lights, and water-volatile heavies. The term "lights" as used herein includes those species with a boiling point below IPA, such as acetone, and "heavies" includes those species with a boiling point above IPA. Water-volatile heavies are those species which, although having a boiling point above IPA, nevertheless are taken off in the overheads as an azeotrope with water. In the preferred embodiment of the present invention wherein the feed 4 is from the Sulfuric Acid Process, such water-volatile heavies include 2,6,8-trimethyl-4-nonanone, 2,6-dimethyl-4-heptanone, and the like.

Preferred operating conditions for catalytic distillation tower 1 is a temperature range of from 150 to 600° F. (about 65 to about 315° C.), more preferably 200–300° F. (about 90 to about 150° C.) and 14.7–1400 PSIA, more preferably 14.7–200 PSIA. In addition, it is preferred that the water/DIPE ratio in the system 1 be kept between about 1:1 and about 25:1, more preferably between 1:1 and 20:1, even more preferably between 2:1 and 10:1, and still more preferably between about 3:1 and 7:1.

Under these preferred operating conditions, when feed 4 is from the Sulfuric Acid Process, the lights normally will be propylene, any $C_4$–$C_5$ olefins, etc. These together with hexenes, $C_9$ and higher olefins will go overhead (5).

About ⅔ of any sec-butyl alcohol and methyl ethyl ketone present will go overhead, along with most of any $C_5$ alcohols and ketones. About 90% of the $C_9$ ethers will also go overhead, together with 80–90% of the $C_{12}$ ethers and 40–60% of any $C_9$ and $C_{12}$ ketones and $C_{15}$–$C_{18}$ ethers. There are also a number of "others", not identified otherwise, but which may be higher olefins, which go overhead to the extent of 80–90%.

Numerous treatments of stream 5 are possible. In a preferred embodiment according to the present invention, the stream 5 is condensed and separated in apparatus 10. Apparatus 10 is preferably a conventional settler which allows for at least two liquid phases with appropriate drawoff lines and an overhead line for removal of vapor, e.g., propylene in stream 7. Apparatus 10 can be either a horizontal or vertical drum with both overall and interface level controllers, as are known per se in the art. The lower phase, taken off as reflux stream 9, contains DIPE, IPA, and water, while the upper phase, taken off as stream 8, would comprise water-insoluble olefins, higher ethers, and ketones, etc.

Reflux stream 9 is recycled back into the catalytic distillation column. It may come into the column at one or more points relative to the trays, preferably from below the trays to about the middle of the column. In the preferred embodiment, reflux stream 9 is returned about in the middle of the array of trays 2.

In the preferred embodiment, initially the IPA in the overhead solubilizes the DIPE, olefins, ethers, etc., into the water phase, but as the total amount of these latter materials builds up, a second (upper) phase will form, which would contain some DIPE and some IPA. This upper phase is sent via stream 8 to a water Wash Tower, or Ether Washer, which is per se known in the art, to recover any IPA. Eventually a purge of a stream containing these byproducts, along with some DIPE, would need to be removed.

In a preferred embodiment, additional IPA is added to column 1 to solubilize DIPE. In another preferred embodiment, some other solubilizing agent may be used, such as γ-butyro-lactone. The addition of such a solubilizing agent may be made to column 1 at one or more points in the column, including by addition to stream 9, but is preferably made from about the middle of the array of trays 2 to above the trays, and more preferably at about the middle of the column, midway between the top and bottom trays (or packing).

By continuous recycle of the lower phase, stream 9, IPA eventually will go out entirely with the bottoms IPA/water stream 11. An alternative would be to send stream 9 to the ether washer, similar to the overhead streams from a heads tower, described more fully below.

Utilizing recycle stream 9, conversion of DIPE to IPA of 90% or better can be achieved, more preferably 99%, and most preferably 99.9%.

IPA is removed from the bottom of the tower 1 through connection 6. As shown in the preferred embodiment of FIG. 1, the IPA/water stream leaves the bottom of the tower and is sent in two directions. The product is withdrawn by stream 11 on level control and sent to the IPA finishing section (e.g., wherein IPA is further purified). The other portion is recycled via stream 12 where it is heated by live steam to the vapor state and returned to the tower, preferably below the trays, such as via an inlet such as 21 shown in FIG. 2. Recirculation can be accomplished either by use of a pump or by a thermosyphon reboiler. In another preferred embodiment shown in FIG. 2, the IPA/water product 23 is removed from the tower bottom and sent only to the Finishing Section via stream 11, and live steam is injected through port 21 directly below the lower tray 22.

Further treatment of stream 11 may accomplished depending on various factors, such as the source of DIPE or the use requirements of the IPA product. Stream 11 may be sent to a heads tower or heads column, where IPA is separated from DIPE and other lights, if present, by extractive distillation with water, and then to the alcohol tower, where a water/IPA azeotrope is separated by azeotropic distillation from water. Such treatment is known per se in the prior art, such as U.S. Pat. No. 2,668,863. An alternative is to by-pass the heads tower and go directly to the alcohol tower. In addition, in series with one or more of the above, the stream 11 may be sent to a reactor to remove odor, e.g., as described in U.S. Pat. No. 4,219,685, and/or then to a dehydration tower, such as described in U.S. Pat. No. 4,161,429.

In yet another preferred embodiment, a conventional heads tower is retrofitted with catalytic packing and/or trays. The heads tower, as described in the immediately preceding paragraph, has a feed containing both IPA and DIPE (along with other impurities depending on the source). One of ordinary skill in the art in possession of the present disclosure could easily retrofit such a column in order to improve the yield of IPA relative to DIPE.

The present inventor has described in detail above a process for the conversion of DIPE to IPA in substantially 100% yield. It will be appreciated that in light of the above teachings, numerous modifications and variations of the present invention are possible. It is therefore to be understood that within the scope of the appended claims, the invention may be practiced otherwise than as specifically described herein.

What is claimed is:

1. A process for hydrolyzing di-isopropyl ether comprising feeding a stream comprising di-isopropyl ether into a distillation column having therein a solid acid catalyst suitable for catalyzing the hydrolysis of di-isopropyl ether to isopropanol, and hydrolyzing said ether to isopropanol.

2. The process according to claim 1, further comprising taking off as bottoms a fraction comprising isopropanol and taking off as overheads a fraction comprising di-isopropyl ether.

3. The process according to claim 1, wherein said feed stream containing di-isopropyl ether is a stream from the catalytic hydration of olefins.

4. The process according to claim 3, wherein said feed stream is from the Indirect Hydration Process.

5. The process according to claim 4, wherein the feed stream is from the Sulfuric Acid Process.

6. The process according to claim 1, wherein the feed stream comprises a mixture of di-isopropyl ether and isopropanol and wherein said distillation column is a retrofitted heads tower.

7. The process according to claim 2, wherein the overheads fraction comprises unreacted di-isopropyl ether and an azeotrope of di-isopropyl ether, water, and isopropanol, and wherein said unreacted di-isopropyl ether and said azeotrope are recycled back into said distillation column.

8. The process according to claim 1, wherein said di-isopropyl ether feed stream enters the distillation column below said catalyst and wherein water is fed into the distillation column above said catalyst.

9. The process according to claim 1, wherein steam and said feed comprising di-isopropyl ether enter the distillation column below said catalyst.

10. The process according to claim 1, wherein said catalyst is selected from the group consisting of an acidic ion exchange resin, supported inorganic acids, acidic alumina, and acidic zeolites.

11. The process according to claim 1, wherein said process is continuous and wherein the conversion of di-isopropyl ether to isopropyl alcohol is substantially 100%.

12. The process according to claim 1, wherein the ratio of water to DIPE in said distillation column is between about 2:1 to about 10:1.

13. In a process for the catalyzed hydration of olefins wherein di-isopropyl ether is produced, the improvement comprising diverting at least a portion of a stream comprising di-isopropyl ether from a recycle stream into a catalytic distillation column, whereby the di-isopropyl ether is hydrolyzed by water in the presence of a suitable catalyst to produce isopropanol.

14. The process according to claim 13, wherein the conversion of di-isopropyl ether to isopropyl alcohol is substantially 100%.

* * * * *